United States Patent
Pelletier et al.

(10) Patent No.: US 10,073,041 B2
(45) Date of Patent: Sep. 11, 2018

(54) OPTICAL COMPUTING DEVICES FOR MEASUREMENT IN CUSTODY TRANSFER OF PIPELINES

(71) Applicant: Halliburton Energy Services, Inc., Houston, TX (US)

(72) Inventors: Michael T. Pelletier, Houston, TX (US); David L. Perkins, The Woodlands, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 22 days.

(21) Appl. No.: 15/303,325

(22) PCT Filed: Dec. 29, 2015

(86) PCT No.: PCT/US2015/067791
§ 371 (c)(1),
(2) Date: Oct. 11, 2016

(87) PCT Pub. No.: WO2017/116411
PCT Pub. Date: Jul. 6, 2017

(65) Prior Publication Data
US 2018/0017500 A1    Jan. 18, 2018

(51) Int. Cl.
*G01N 21/3504* (2014.01)
*G01N 33/28* (2006.01)
(Continued)

(52) U.S. Cl.
CPC ......... *G01N 21/85* (2013.01); *G01N 21/3504* (2013.01); *G01N 21/3577* (2013.01);
(Continued)

(58) Field of Classification Search
CPC .. B65G 43/08; B65G 53/66; B65G 2203/044; B65G 47/31; G01N 21/59; G01N 21/31; G01N 21/85; E21B 49/08; G06E 3/001
See application file for complete search history.

(56) References Cited

U.S. PATENT DOCUMENTS 3,309,308 A    3/1967  Schad
3,322,135 A *  5/1967  Watson ............... G01F 15/075
                                                      137/113
(Continued)

FOREIGN PATENT DOCUMENTS

WO    8802476 A1    4/1988

OTHER PUBLICATIONS

ISR/WO for PCT/US2015/067791 dated Sep. 29, 2016.

*Primary Examiner* — Sang Nguyen
(74) *Attorney, Agent, or Firm* — McDermott Will & Emery LLP

(57) ABSTRACT

A device including an integrated computational element (ICE) positioned to optically interact with electromagnetic radiation from a fluid and to thereby generate optically interacted radiation corresponding to a characteristic of the fluid, and a method for using the system are provided. The device includes a detector positioned to receive the optically interacted radiation and to generate an output signal proportional to an intensity of the optically interacted radiation. And the device further includes a processor positioned to receive the output signal and to determine the characteristic of the fluid. The device is coupled to a controller configured to provide instructions to a transfer system for storage and readout.

20 Claims, 8 Drawing Sheets

(51) Int. Cl.
*G06F 3/00* (2006.01)
*G01N 21/85* (2006.01)
*G01N 21/3577* (2014.01)
*G06E 3/00* (2006.01)

(52) U.S. Cl.
CPC .............. *G01N 33/28* (2013.01); *G06E 3/001* (2013.01); *G06E 3/008* (2013.01)

(56) References Cited

U.S. PATENT DOCUMENTS

| | | | |
|---|---|---|---|
| 5,006,785 A | 4/1991 | Revus et al. | |
| 5,103,181 A | 4/1992 | Gaisford et al. | |
| 6,234,250 B1* | 5/2001 | Green | E21B 47/0003 166/250.03 |
| 7,150,184 B1 | 12/2006 | Scott et al. | |
| 8,619,256 B1* | 12/2013 | Pelletier | E21B 47/0005 356/335 |
| 8,739,635 B2 | 6/2014 | Bruno et al. | |
| 8,908,165 B2* | 12/2014 | Tunheim | G01N 21/85 356/73 |
| 9,013,698 B2* | 4/2015 | Freese | G01N 21/59 356/300 |
| 9,816,626 B1* | 11/2017 | DeBlieck | F16K 11/044 |
| 2004/0112122 A1 | 6/2004 | Steward | |
| 2013/0032340 A1 | 2/2013 | Freese et al. | |
| 2013/0033702 A1 | 2/2013 | Tunheim et al. | |
| 2013/0284898 A1* | 10/2013 | Freese | G01N 21/17 250/208.2 |
| 2014/0324366 A1 | 10/2014 | Ljungdahl et al. | |
| 2016/0327211 A1* | 11/2016 | Hammond | F17D 5/02 |
| 2017/0217689 A1* | 8/2017 | Holden | B65G 43/08 |

* cited by examiner

OPTICAL COMPUTING DEVICES FOR MEASUREMENT IN CUSTODY TRANSFER OF PIPELINES

BACKGROUND

Current methods for determining the quality of an oil or natural gas product flowing in a pipeline involve direct sampling of the liquid or gas to perform a detailed chemical analysis such as gas chromatography, liquid chromatography, or the like. These point measurements are logistically difficult and costly, and introduce an inherent time-delay between two consecutive measurement points. In addition, some of the current testing techniques involve the use of hazardous chemicals. Furthermore, the complexity of the chemical measurements makes it difficult, if not impossible, to correlate a measured characteristic of a fluid at a certain point with the actual value of the characteristic of the fluid at that point in real time.

To determine certain deleterious characteristics such as the water content in a crude oil pipeline, some approaches include capacitive electrical measurements, or microwave absorption measurements. For gases, current industry technology includes density meters. However, these measurements tend to be slow and imprecise, leading to high recycling rates for improving the quality of the oil or natural gas product, and thereby reducing the throughput of the system.

BRIEF DESCRIPTION OF THE DRAWINGS

The following figures are included to illustrate certain aspects of the exemplary embodiments described herein, and should not be viewed as exclusive embodiments. The subject matter disclosed is capable of considerable modifications, alterations, combinations, and equivalents in form and function, as will occur to those skilled in the art and having the benefit of this disclosure.

In the figures, elements having the same or similar reference numeral share the same or similar functionality and description, unless stated otherwise.

DETAILED DESCRIPTION

Figure 1:
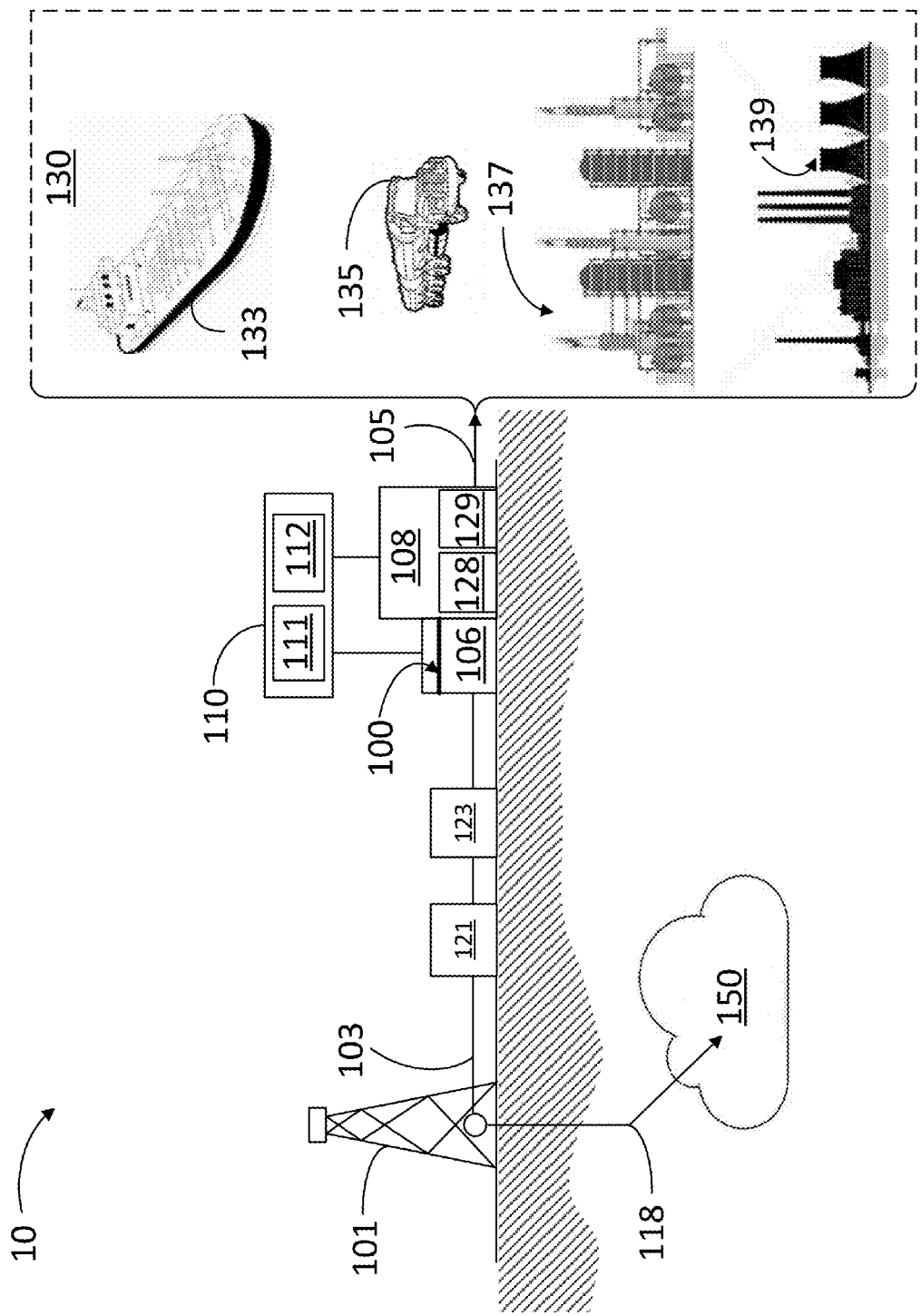
FIG. 1 illustrates an oil and gas production configuration including a lease automatic custody transfer (LACT) system.

The exemplary embodiments described herein relate to optical computing devices and methods for monitoring fluid flows and, in particular, to systems and methods for determining the flow characteristics and condition of liquids and gases in the oil and gas industry. Methods and systems consistent with the present disclosure are able to characterize the flow by "seeing" the liquid or gas as it flows through a pipeline in real time. Being able to monitor the liquid or gas in real time enables intelligent adjustment of fluid properties, such as flow rate, water content, gaseous content, or contaminant content. As will be appreciated, this may increase the value of the hydrocarbon product transported through the pipeline, and reduce costs, hazards, and maintenance associated with transportation.

Embodiments disclosed herein include devices and methods for measuring crude oil/natural gas during legal custody transfer from a production company (e.g., the "producer") to a contracting pipeline company. Devices as disclosed in the present disclosure may be purchased or temporarily leased by oil and gas production companies, e.g., for performing extended drill stem tests (DST). For example, measuring the fluid flow in a pipeline may help a gas production company during the DST while transferring fluids into a pipeline to reduce and control flaring events in the pipeline, downstream from the measurement point.

Embodiments consistent with the present disclosure include a sensor to measure characteristics of a fluid at a lease automatic custody transfer (LACT) point. A LACT point occurs when the production fluids (e.g., crude oil or natural gas) are transferred from the producer to either a pipeline contractor or to a pipeline owned by a refiner. The measured characteristics of a fluid are selected from those that may reduce the value of a hydrocarbon product included in the fluid, or that make it excessively costly to pump the fluid down a pipeline. The hydrocarbon product may be a liquid (e.g., crude oil), or a gas (e.g., natural gas). The producer and the pipeline contractor agree on a set of specifications or quality parameters that the hydrocarbon product desirably meets. The producer desires that the fluid flow be no lower than established specifications, and thereby minimize costs of ensuring that the fluid is up to specification. The pipeline contractor, who buys the hydrocarbon product from the producer, wants to maximize gains by certifying that the hydrocarbon product is better than, or equal to the specification and ensure that the transportation cost is spent mostly on high value hydrocarbon product. Accordingly, at the LACT point the producer and the pipeline contractor may decide on the value of the measured hydrocarbon product. Producer and pipeline contractor may also decide whether further treatment of the pipeline flow is desirable to improve quality parameters of the hydrocarbon product. Further, producer and pipeline contractor may decide not to proceed with the transaction based on safety, cost, or other considerations.

Optical computing devices disclosed herein provide rapid analysis of at least one characteristic of a liquid or a gas (e.g., water content, gas-oil-ratio -GOR-, $CO_2$ content, $H_2S$ content, and the like) with little or no sampling preparation. Additionally, because the analysis is rapid, multiple measurements may be obtained to reduce error. In some embodiments, an optical computing device may be configured to specifically detect and/or measure a particular characteristic of a liquid or a gas, including mixtures of many different components, in different phases (i.e., solid, liquid or gas). The characteristic of the liquid or gas may be the presence and concentration of a certain analyte in a mixture of components.

As used herein, the term "characteristic" refers to a chemical, mechanical, or physical property (quantitative or qualitative) of a material of interest (e.g., a liquid, a gas or an analyte thereof). As used herein, the term "analyte" refers to a chemical component. The term analyte encompasses chemical components that are at least one of: present in the material of interest, may be added to the material of interest, involved in a chemical reaction (e.g., reagents and products) transpiring within the material of interest, and not involved in a chemical reaction transpiring within the material of interest. Illustrative characteristics of a material of interest that can be monitored with the optical computing devices disclosed herein can include, for example, chemical composition (e.g., identity and concentration in total or of individual analytes), contaminant content, pH, viscosity, density, ionic strength, salt content, porosity, opacity, bacteria content, particle size distribution, color, temperature, hydration level, oxidation state, and the like. Moreover, the phrase "characteristic of interest" may be used herein to refer to a characteristic of a material of interest.

As used herein, the term "electromagnetic radiation" refers to radio waves, microwave radiation, infrared and near-infrared radiation, visible light, ultraviolet light, X-ray radiation and gamma ray radiation.

As used herein, the term "optical computing device" refers to an optical device that receives an input of electromagnetic radiation from a substance or fluid, and produces an output signal proportional to a property of interest of the sample. The optical computing device includes a processing element and an optical detector arranged within the optical computing device. The processing element may be, for example, an integrated computational element (ICE) used in the optical computing device. As discussed in detail below, the ICE optically interacts with and changes the electromagnetic radiation from a substance or fluid, and outputs a modified electromagnetic radiation to an optical detector. The optical computing device is designed such that the output of the detector can be correlated to at least one characteristic of the substance being measured or monitored. The input electromagnetic radiation to the processing element can be backscattered electromagnetic radiation, reflected electromagnetic radiation, diffuse reflected electromagnetic radiation, transmitted electromagnetic radiation, and/or dispersed electromagnetic radiation. Whether the optical computing device analyzes reflected or transmitted electromagnetic radiation may depend on the structural parameters of the optical computing device as well as other considerations known to those skilled in the art. In addition, emission and/or scattering by the substance, for example via fluorescence, luminescence, Raman scattering and Rayleigh scattering, can be monitored by the optical computing devices.

As used herein, the term "optically interact" or variations thereof refers to the reflection, transmission, scattering, diffraction, or absorption of electromagnetic radiation either on, through or from one or more processing elements (i.e., integrated computational elements). Accordingly, optically interacted light refers to electromagnetic radiation that has been reflected, transmitted, scattered, back scattered, diffusely reflected, diffracted, or absorbed by, emitted, or re-radiated, for example, using the integrated computational elements, but may also apply to interaction with the a liquid or a gas in a pipeline flow.

The presently described optical computing devices combine the advantage of the power, precision, and accuracy associated with laboratory spectrometers, while being extremely rugged and suitable for field use. Furthermore, optical computing devices consistent with the present disclosure can perform calculations in real-time or near real-time without the need for time-consuming fluid sampling. In this regard, in some embodiments the optical computing devices detect and analyze particular characteristics of interest. As a result, interfering or undesirable signals are discriminated from those of interest by appropriate configuration of the optical computing devices. Thus, optical computing devices as disclosed herein provide rapid responses regarding the characteristic of interest based on a detector output. In some embodiments, the detector output is a voltage indicative of the magnitude of the characteristic of interest. The foregoing advantages and others make the optical computing devices particularly well suited for field use.

In some embodiments, optical computing devices detect not only the composition and concentrations of an analyte in a material of interest, but also determine physical properties and other characteristics of the material of interest based on the interacted electromagnetic radiation received from the substance. For example, optical computing devices can determine the concentration of an analyte and correlate the determined concentration to a characteristic of the material of interest by using suitable processing means. As will be appreciated, optical computing devices as disclosed herein can detect as many characteristics as desired for a given material of interest. Suitable processing and detection ICEs for each characteristic of interest may be incorporated into an optical computing device to monitor multiple characteristics of interest (e.g., the concentration of an analyte, the pressure, or the temperature).

In some embodiments, the properties of the material of interest can be determined using a combination of characteristics of interest (e.g., a linear, non-linear, logarithmic, and/or exponential combination). Accordingly, the more characteristics detected and analyzed using the optical computing devices, the more accurately the properties of the material of interest will be determined. For example, properties of a liquid or gas that may be determined using optical computing devices described herein may include, but are not limited to, the absolute concentration of an analyte, the relative ratios of two or more analytes, the presence or absence of an analyte, and the like, and any combination thereof. The characteristic of the material of interest may be a fluid property such as a vapor pressure, a dew point, a bubble point, a density, a velocity, or any other thermodynamic property of a liquid or gas flow.

Optical computing devices as described herein utilize electromagnetic radiation to perform calculations, as opposed to the hardwired circuits of conventional electronic processors. When electromagnetic radiation interacts with a material of interest, unique physical and chemical information about the material of interest may be encoded in the electromagnetic radiation that is backscattered, reflected, or radiated from, or transmitted through, the material of interest. This information is the spectral "fingerprint" of the material of interest. Optical computing devices described herein are capable of extracting the information of the spectral fingerprint of multiple characteristics of a material of interest (e.g., a liquid or gas flow or an analyte thereof), and converting that information into a detectable output regarding the overall properties of the monitored material of interest. That is, through suitable configurations of the optical computing devices, electromagnetic radiation associated with characteristics of interest can be separated from electromagnetic radiation associated with other components of the material of interest in order to estimate the properties (e.g., reactivity) of the monitored substance (e.g., a liquid or gas flow or an analyte thereof) in real-time or near real-time.

Embodiments disclosed herein use ICE technology during a lease automatic custody transfer at a LACT point. Accurate measurement of the hydrocarbon product at the LACT point is important because the producer's revenue is based on that measurement. Depending on whether or not the hydrocarbon product contains other compounds, such as water, $H_2S$, or $CO_2$, its value can vary dramatically. On the other hand, pipeline contractors may be concerned about contaminating compounds because of safety issues and their damaging potential to pipeline infrastructure. Also, pipeline contractors realize the deleterious effect of contaminants on the value of the hydrocarbon product for resale to refiners, power plant operators, and the like.

Producers have an interest in ensuring that production volume is accurately measured during custody transfer because the measured volume directly affects the revenue received for the production fluids. The pipeline contractors have an interest in ensuring that the production volume is accurately measured at the LACT point because the measured volume directly affects the global price of crude oil and to reduce transportation cost of the hydrocarbon product along the pipeline. Accordingly, it is desirable that transportation costs be incurred on valued product and not on heavy, hazardous, or difficult to transport contaminants adding drag to the flow. In addition, the producer and the pipeline contractor each benefit from an accurate account of contaminants whose presence or absence directly affects the value of the hydrocarbon product and which can pose significant safety risks to pipeline system and personnel. ICE units in the optical computing devices can be designed to detect parameters of economic interest with low error bands with a relatively high sensitivity.

Table 1 shows the revenue loss in an oil and gas production configuration for a 1% crude oil flow metering error using a mechanical system for measurement. Data in Table 1 includes a $50/bbl, and $102/bbl price points for crude oil and it does not indicate revenue loss due to the presence or amounts of contaminants and other compounds contained in the crude oil. Data as shown in Table 1 indicate a basis for establishing the value that the disclosed embodiments of an optical computing device and methods for measurement may have to potential clients, be it a producer, a pipeline contractor, a consumer of hydrocarbon products, or all of the above.

TABLE 1

ANNUAL REVENUE LOSSES FROM 1% METERING ERROR

| Daily Lease | Annual Lost Revenue at 1% Metering Error | |
| --- | --- | --- |
| Production (bbl) | 2005 ($50/bbl) | 2014 ($102/bbl) |
| 500 | $91,250.00 | $186,150.00 |
| 1,000 | $182,500.00 | $372,300.00 |
| 2,000 | $273,750.00 | $558,450.00 |
| 3,000 | $547,500.00 | $1,116,900.00 |

In a first embodiment, a device includes an integrated computational element (ICE) positioned to optically interact with electromagnetic radiation from a fluid and to thereby generate optically interacted radiation corresponding to a characteristic of the fluid. The device includes a detector positioned to receive the optically interacted radiation and to generate an output signal proportional to an intensity of the optically interacted radiation. And the device may further include a processor positioned to receive the output signal and to determine the characteristic of the fluid. In some embodiments, the device is coupled to a controller configured to provide instructions to a transfer system for storage and readout. Accordingly, the transfer system may be a LACT system configured to modify a flow and a composition of the fluid when the characteristic of the fluid is below a quality parameter.

In a second embodiment, a method includes optically interacting a fluid flow in a production pipeline with an ICE to generate optically interacted radiation. The method includes producing an output signal proportional to an intensity of the optically interacted radiation, and correlating the output signal with a characteristic of the fluid. In some embodiments, the method includes modifying the fluid to maintain a quality parameter according to the characteristic of the fluid, and transferring the fluid from a production pipeline to a contractor pipeline according to the quality parameter.

In a third embodiment, a non-transitory, computer readable medium stores commands which, when executed by a processor in a measurement system including an optical computing device cause the measurement system to perform a method. The method includes optically interacting a fluid in a production pipeline with an ICE to generate optically-interacted radiation. The method also includes producing an output signal proportional to an intensity of the optically interacted radiation, correlating the output signal with a characteristic of the fluid, and modifying the fluid to maintain a quality parameter according to the characteristic of the fluid and to reduce a maintenance cost according to the characteristic of the fluid. In some embodiments, the method further includes transferring the fluid from a production pipeline to a contractor pipeline according to the quality parameter.

FIG. 1 illustrates an oil and gas production configuration 10 including a lease automatic custody transfer (LACT) system 108. Configuration 10 also includes a production rig 101 reaching into a reservoir 150 through a wellbore 118 to produce hydrocarbons into a production pipeline 103. The hydrocarbons may be in multiple fluid phases: liquid (e.g., crude oil), gas (e.g., natural gas including methane butane, propane, $C_3$-$C_5$ hydrocarbons, and other hydrocarbons), or a mixture of liquid and gas phases (e.g., oil with natural gas bubbles, natural gas with entrained liquid -mist-). After production, the material goes through a bulk phase separator 121 and into a holding tank 123. Bulk phase separator 121 separates a liquid phase hydrocarbon and a gas phase hydrocarbon from the fluid flow in production pipeline 103. In some embodiments, bulk phase separator 121 is configured to have gaseous hydrocarbon products flowing down production pipeline 103. In some embodiments bulk phase separator 121 is configured to have liquid hydrocarbon products (e.g., crude oil) flowing down production pipeline 103. Holding tank 123 pumps the fluid to and LACT system 108 where it is distributed accordingly. In some embodiments, a production pipeline 103 using natural gas may operate at a flow pressure of 500-800 pounds per square-inch (psi) after separator 121. The natural gas may go directly into LACT system 108 or to a smaller pressure separator 128 before going into a compressor 129 in LACT system 108 and into contractor pipeline 105.

An optical computing device 106 is disposed at or near LACT system 108, which couples production pipeline 103 to a contractor pipeline 105. LACT system 108 is considered to be positioned at a LACT point, which consists of a measurement point where the amount, quality, and value of hydrocarbon product within production pipeline 103 is transferred to contractor pipeline 105. Accordingly, the hydrocarbon product in contractor pipeline 105 is considered to be legally under the care of a contractor. Thereafter, the hydrocarbon product may be transferred to a variety of destination points 130 including, but not limited to, transportation vehicles, such as a tanker ship 133, a tanker truck 135, or a facility, such as a storage tank in a refinery 137, or a power plant 139. In the case of a power plant 139, a density measurement of the hydrocarbon product is directly related to the energy content of the product and thus the operational efficiency of the power plant 139.

In some embodiments, LACT system 108 may include a metering system (e.g., flow meter, pressure meter, temperature meter, and the like), a recycle valve, and a shut-off valve. Further, LACT system 108 may be configured to actuate the shut-off valve to a closed position when the hydrocarbon product has a quality parameter that measures below a predetermined or preferred specification. In such configurations, the flow into contractor pipeline 105 may be stopped altogether and the recycle valve in LACT system 108 may be opened to direct the fluid flow into a de-contamination unit associated with LACT system 108.

In some embodiments, optical computing device 106 is configured to measure a desired characteristic of the fluid, such as a chemical composition or a physical condition of the flow. In some embodiments optical computing device 106 is configured to measure a bubble content in a liquid, a mist content in a gas, or the density, temperature, pressure, viscosity, or velocity of the fluid. Optical computing device 106 may include an integrated computational element (ICE) 100 for measuring the desired fluid characteristic. The use of ICE 100 provides increased accuracy in the measurement of volume, composition, and compounds contained in the crude oil/natural gas mixture during legal custody transfer. Due to the precision of ICE 100, optical computing device 106 may be designed to detect characteristics of the fluid that have a direct impact on economic interests with small error bands over relatively small ranges of values. In addition, ICE 100 enables real-time measurements of the fluid flowing through production pipeline 103, which can be processed electronically by a controller 110 to obtain a comprehensive analysis of the fluid flow and the product quality. In that regard, optical computing device 106 may include a plurality of ICEs, each designed to target a specific fluid characteristic.

Controller 110 may include a processor 111 and a memory 112. Processor 111 executes commands stored in memory 112 and causes controller 110 to perform steps in methods described herein. In some embodiments, controller 110 is communicably coupled to optical computing device 106 and is configured to receive data from and provide commands to optical computing device 106. Controller 110 may also be communicably coupled to LACT system 108 and may be configured to receive data from and provide commands to LACT system 108. The coupling of controller 110 with optical computing device 106 and with LACT system 108 may be through an electrical cable, an optical fiber, or via a wireless data transmission communication protocol. In that regard, controller 110 may be remote to the specific location of optical computing device 106 and LACT system 108 (i.e., LACT point). Moreover, in some embodiments, controller 110 may couple to a plurality of optical computing devices 106 and LACT systems 108 placed in multiple locations remote from each other. Controller 110 may provide commands whether to modify fluid conditions, recycle the fluid flow, or allow the fluid flow to transfer to contractor pipeline 105.

In some embodiments, a third party determines a ranking of hydrocarbon product according to measured values of the quality parameters. In any event, the quality parameters may be objectively assessed, in real-time, by optical computing device 106. In some embodiments, producer and pipeline contractor may agree to modify the quality parameters of the hydrocarbon according to measurements of optical computing system 106. Controller 110 may instruct LACT system 108 to adjust a flow configuration and maintain the value of a quality parameter of the hydrocarbon product within a pre-determined range.

In some embodiments, ICE 100 detects at least one or multiple analytes that can negatively affect a value of the hydrocarbon product extracted from reservoir 150. Because maximum allowable amounts will be established for these compounds, controller 110 may reject production fluids through production pipeline 103. In some embodiments controller 110 may adjust the value assessment of the hydrocarbon product, depending on the analytes present and whether or not the amount of analytes present exceed a maximum allowable limit. For example, some analytes may raise safety concerns for the facilities and personnel in oil and gas production configuration 10, and thus the operation of production rig 101 may be stopped altogether. Potential analytes targeted by optical computing device 106 may include water, $H_2S$, $CO_2$, and nitrogen, among others. At least some of these substances, in addition to lowering the value of the transported product and adding to the transporting costs, may corrode and cause maintenance and safety issues in pipelines 103 and 105. By choosing an appropriately designed ICE 100, optical computing device 106 may increase the list of fluid characteristics desired for measurement, such as additional unacceptable components for screening before or at the LACT point.

In some embodiments, the total amount of water vapor present in crude oil may be a relevant quality parameter. Water vapor in crude oil has a tendency to form gaseous hydrates in solution. Gaseous hydrates may become a major safety issue by plugging valves and forming hazardous fumes for maintenance employees. In some embodiments, optical computing device 106 measures the total amount of water vapor present in crude oil, before allowing the hydrocarbon product to flow into contractor pipeline 105.

During hydrocarbon extraction in production rig 101, and transmission in production pipeline 103, chemicals added to maintain and improve the operation of the fluid and drilling system may contaminate the hydrocarbon product. Depending on the amount of additives present in production pipeline 103, these may be detrimental to the pipeline system and even to the crude oil itself. These additives can include anti-foam agents, chlorinated agents, glycol, and surfactants. Further, in the case of crude oil production, some additives may include chemistries used for de-hydration of the liquid oil, such as ethylene glycol, amines, and other chemicals. Optical computing device 106 may be configured to generate an output signal configured to alert controller 110 of the presence and amount of additives in the hydrocarbon product flowing through production pipeline 103. In some embodiments, controller 110 may be configured to determine whether the production fluid can enter contractor pipeline 105 "as is," or whether it should be diverted to a recycle unit or procedure in LACT system 108 before re-entering pipeline 105.

In embodiments where production pipeline 103 and contractor pipeline 105 contain a crude oil flow, it may be desirable to obtain a measure of vapor pressure for the crude oil. To measure vapor pressure, optical computing device 106 may be configured to measure a concentration of methane, ethane, propane, and C3-C5 hydrocarbons, which are the major contributors to vapor pressure. Thus, in some embodiments controller 110 correlates an amount of gas in the oil measured by optical computing device 106 with a known temperature and fluid pressure determined by LACT system 108 to determine the vapor pressure. The vapor pressure relative to the fluid pressure determines the bubble point of the fluid, which is the temperature at which gas bubbles start forming in the liquid. In general, the higher the vapor pressure, the lower the bubble point of the liquid, and the lower the vapor pressure the higher the bubble point of the liquid, for a given fluid pressure. Accordingly, based on a vapor pressure estimate obtained with optical computing device 106, LACT system 108 may set flow conditions to avoid formation of gas bubbles, such as reducing the temperature or increasing the pressure of the flow.

In some embodiments, temperature and pressure conditions may be modified by LACT system 108 using heaters to raise the temperature, coolers to lower the temperature, compressors to raise fluid pressure, and pumps to lower fluid pressure. The quality parameter related to vapor pressure in a crude oil flow may vary depending on geographic and seasonal conditions of pipelines 103 and 105. For example, a quality parameter may include a vapor pressure value of about 6 psi or lower for crude oil in summer of a mild tempered region (e.g., Mediterranean weather). On the other hand, a quality parameter may include a vapor pressure of about 12 psi or lower for crude oil in the northern California winter. Crude oil flows having higher vapor pressure than indicated by the quality parameter may induce a pipeline explosion, if no remedial action is taken. More generally, selecting a quality parameter for the hydrocarbon product may include an environmental characteristic of the pipeline. Indeed, whether the pipeline is exposed to high or low temperatures, or crosses through areas where the temperature varies strongly between day and night, or through different season in the year, may determine the values that LACT system 108 uses do establish a quality parameter. In embodiments consistent with the present disclosure, quality parameters as determined herein may be considered also in static fluid conditions such as in a reservoir, tank or container of the hydrocarbon product (e.g., holding tank 123, tanker ship 133, tanker truck 135, a storage tank in refinery 137, or the like).

In some embodiments, a quality parameter is the GOR. In field flow lines it may be desirable that the GOR have a value of one (equal volume of oil and gas under standard pressure and temperature conditions) or less, for transferring a crude oil into contractor pipeline 105. In Oil pipeline applications it is desirable to have the GOR substantially below one. In embodiments where natural gas is being transported, a GOR of 200 or more may be a desired quality parameter for transfer to contractor pipeline 105. For example, in some Gas pipeline operations it is desirable to keep a GOR substantially above 20,000 (twenty thousand).

While FIG. 1 illustrates production rig 101 fluidically coupled to production pipeline 103 and to contractor pipeline 105, in some embodiments optical computing device 106, LACT system 108 (i.e., the LACT point) may be placed where a single producer delivers a discrete amount of hydrocarbon product to a potential buyer, or a buyer under a contract. In some embodiments, the LACT point may be a point of transfer of the hydrocarbon product to any one of destination points 130, such as tanker ship 133, truck 135, refinery 137, or power plant 139.

Some embodiments include an optical computing device 106 configured for natural gas analysis, as follows. A quality parameter of interest in natural gas may be nitrogen content, Mercaptan (Methanethiol) content, and content of analytes that are not combustible such as $H_2S$, water, or any other liquids (including oil mist), ethylene glycol, amines, and other chemicals used to de-hydrate the hydrocarbon product. In some embodiments a nitrogen content of less than 20-25% per volume may be desired for the natural gas product delivered to contractor pipeline 105

Information about the specific gravity or density of the gas also indicates a fuel value. In some embodiments, a quality parameter may be the amount of natural gas provided, expressed in standard cubic feet (SCF). In other embodiments, a quality parameter for natural gas may be the "energy content" of the product. That is, the heat generated upon combustion of a given mass of the product. A measure for energy content may be expressed in British thermal units (BTU), wherein one BTU is the energy needed to heat one pound of water by one degree Fahrenheit. Accordingly, the content of combustible analytes in the gas flow enables a determination of the BTU quality parameter of the natural gas. Combustible analytes in the natural gas may include any one of methane, ethane, propane, C3-C5 hydrocarbons, and other combustible analytes.

In some embodiments, the content of heavy analytes in the natural gas is another quality parameter. The molecular weight of analytes in the natural gas is important to both the producer and the pipeline contractor. For example, a gas with a heavier molecular weight than methane and ethane such as butane, propane, or other components may condense out of the gas as the pipeline cools in the winter months. The condensate can create safety issues in a gas pipeline. Consequently, pipeline contractors may determine a quality parameter more tolerant of heavier molecular weight for flowing natural gas in summer months and a quality parameter more restrictive of analytes with higher molecular weight in winter months.

More generally, in some embodiments a quality parameter may be determined according to the dew point of the natural gas. Optical computing device 106 may be configured to provide a measurement of the concentration of different analytes in the gas flow, so that a minimum dew point for the gas is determined. The dew point of a gas is the temperature at which a drop of liquid is condensed out of the gas, at a given gas pressure. In some configurations, a drop of liquid is formed in a gas flow when the gas pressure is higher than the vapor pressure of the liquid phase of the analyte at the gas flow temperature. Accordingly, if the gas pressure, temperature, and analyte concentration are known, the dew point may be determined. To avoid condensation, controller 110 may cause LACT system 108 to perform preventive steps such as: reduce gas pressure, increase gas temperature, increase flow rate, reduce analyte concentration, or any combination thereof. According to their relative concentrations and molecular weight, different analytes may have different dew points in the gas flow. For example, heavier molecules (e.g., $C_3$-$C_5$ hydrocarbons) may have higher dew points than lighter molecules (e.g., methane or ethane) at the same gas flow pressure. If the minimum dew point from among the different analytes present is higher than a desirable quality factor determined according to the season or the environmental conditions in the geography traversed by the pipeline, controller 110 may determine that the gas be re-circulated to LACT system 108 so that propane or the condensing component is removed from the gas. One option may be to introduce an additive in the gas in order to reduce the dew point.

Figure 2:
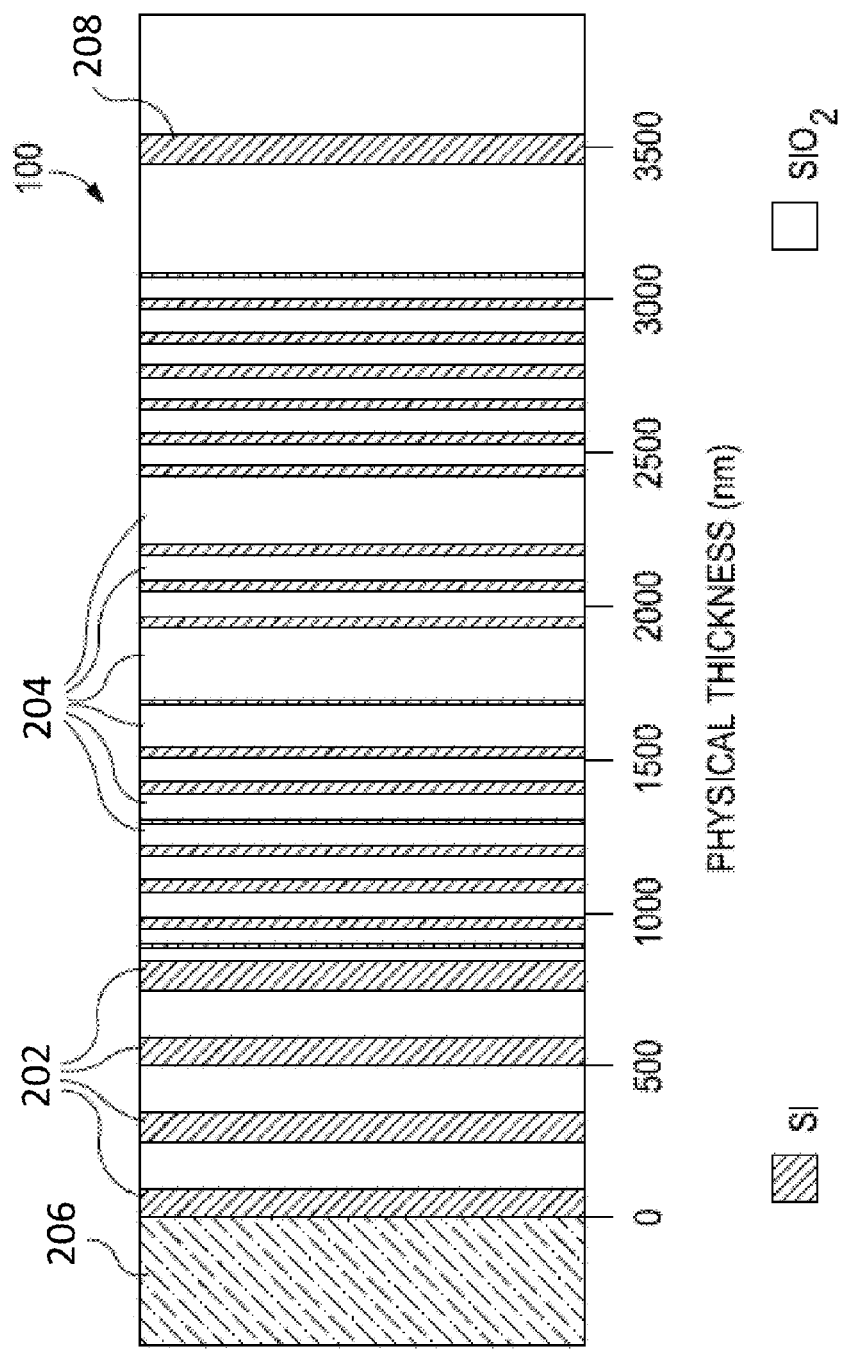
FIG. 2 illustrates an exemplary integrated computational element (ICE) for use in an optical computing device.

FIG. 2 illustrates an exemplary ICE 100 suitable for use in the optical computing devices used in systems and methods described herein. As illustrated, ICE 100 may include a plurality of alternating layers 202 and 204, such as silicon (Si) and $SiO_2$ (quartz), respectively. In general, these layers 202, 204 consist of materials whose index of refraction is high and low, respectively. Other examples might include niobia and niobium, germanium and germania, MgF, $SiO_x$, and other high and low index materials known in the art. An optical substrate 206 provides support to layers 202, 204, according to some embodiments. In some embodiments, optical substrate 206 is BK-7 optical glass. In other embodiments, optical substrate 206 may be another type of optical substrate, such as quartz, sapphire, silicon, germanium, zinc selenide, zinc sulfide, or various plastics such as polycarbonate, polymethylmethacrylate (PMMA), polyvinylchloride (PVC), diamond, ceramics, combinations thereof, and the like.

At the opposite end (e.g., opposite optical substrate 206 in FIG. 2), ICE 100 may include a layer 208 that is generally exposed to the environment of the device or installation. The number of layers 202, 204 and the thickness of each layer 202, 204 are determined from the spectral attributes acquired from a spectroscopic analysis of a characteristic of interest of a sample or fluid, using a conventional spectroscopic instrument. The spectrum of interest of a given characteristic of interest typically includes any number of different wavelengths. The exemplary ICE 100 in FIG. 2 does not in fact represent any particular characteristic of interest, but is provided for purposes of illustration only. Consequently, the number of layers 202, 204 and their relative thicknesses, as shown in FIG. 2, bear no correlation to any particular characteristic of interest. Nor are layers 202, 204 and their relative thicknesses necessarily drawn to scale, and therefore should not be considered limiting of the present disclosure. Moreover, those skilled in the art will readily recognize that the materials that make up each layer 202, 204 (i.e., Si and $SiO_2$) may vary, depending on the application, cost of materials, and/or applicability of the materials to the monitored substance.

In some embodiments, the material of each layer 202, 204 can be doped or two or more materials can be combined in a manner to achieve the desired optical characteristic. In addition to solids, ICE 100 may also contain liquids and/or gases, optionally in combination with solids, in order to produce a desired optical characteristic. In the case of gases and liquids, ICE 100 can contain a corresponding vessel (not shown), which houses gases or liquids. Exemplary variations of ICE 100 may also include holographic optical elements, gratings, piezoelectric, light pipe, digital light pipe (DLP), variable optical attenuators, and/or acousto-optic elements, for example, that can create transmission, reflection, and/or absorptive properties of interest.

Layers 202, 204 exhibit different refractive indices. By properly selecting the materials of layers 202, 204, their relative thicknesses and spacing ICE 100 may be configured to selectively pass/reflect/refract predetermined fractions of electromagnetic radiation at different wavelengths. Each wavelength is given a predetermined weighting or loading factor. The thickness and spacing of layers 202, 204 may be determined using a variety of approximation methods from the spectrograph of the characteristic of interest. These methods may include inverse Fourier transform (IFT) of the optical transmission spectrum and structuring ICE 100 as the physical representation of the IFT. The approximations convert the IFT into a structure based on known materials with constant refractive indices.

The weightings that layers 202, 204 of ICE 100 apply at each wavelength are set to regression weightings described with respect to a known equation, or data, or spectral signature. Briefly, ICE 100 may be configured to perform the dot product of the input light beam into ICE 100 and a desired loaded regression vector represented by each layer 202, 204 for each wavelength, the regression vector associated with the characteristic of interest. As a result, the output light intensity of ICE 100 is associated with the characteristic of interest. In yet other embodiments. Weighting layers 202 and 204 in ICE 100 are selected such that light optically interacted with the fluid and with ICE 100 is disassociated with the characteristic of interest. For example, in some embodiments the thickness and number of weighting layers 202 and 204 may be selected so that ICE 100 performs the dot product of the input light beam into ICE 100 and a loaded regression vector associated with a second characteristic of the fluid other than the characteristic of interest. Moreover, in some embodiments, the thickness and number of layers 202 and 204 may be determined so that an intensity of a light optically interacted with the fluid and with ICE 100 is positively or negatively correlated to the characteristic of interest. Accordingly, in such embodiments the intensity of the light optically interacted with the fluid and with ICE 100 may be proportional to the desired characteristic of the fluid (positive correlation) or inversely proportional to the desired characteristic of the fluid (negative correlation). Furthermore, some embodiments may include at least one ICE associated with the characteristic of interest and at least one ICE disassociated with the characteristic of interest.

Figure 3:
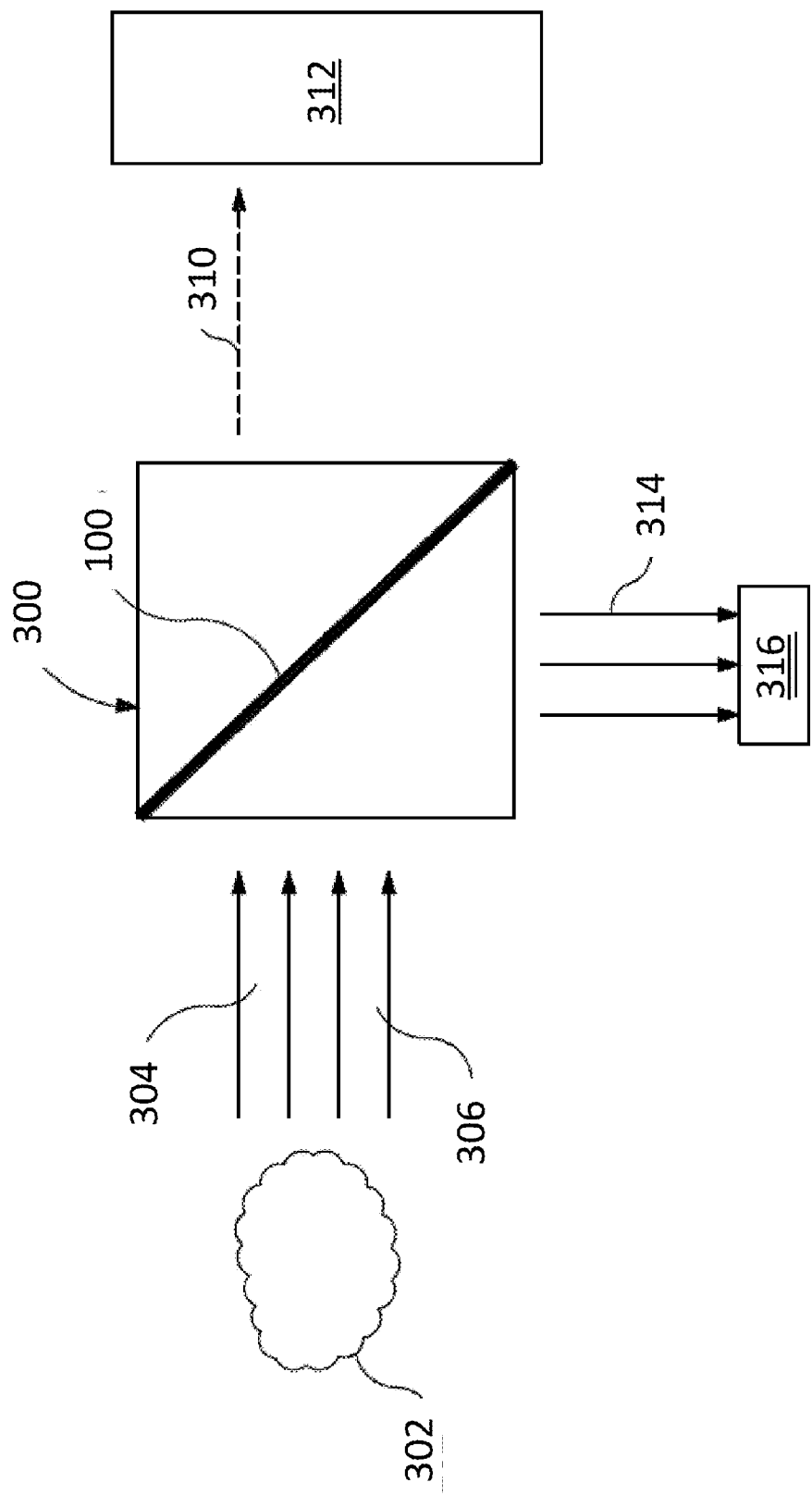
FIG. 3 is a block diagram non-mechanistically illustrating how an optical computing device distinguishes electromagnetic radiation related to a characteristic of interest from other electromagnetic radiation.

FIG. 3 is a block diagram that non-mechanistically illustrates how an optical computing device 300 is able to distinguish electromagnetic radiation related to a characteristic of interest from other electromagnetic radiation. As shown in FIG. 3, illumination by incident electromagnetic radiation induces an output of electromagnetic radiation from a liquid or gas 302 (e.g., optically interacted radiation), some of which is electromagnetic radiation 304 corresponding to the characteristic of interest and some of which is background electromagnetic radiation 306 corresponding to other characteristics of the liquid or gas 302. In some embodiments, liquid or gas 302 may include one or more characteristics of interest that may correspond to one or more analytes in liquid or gas 302. Optical computing device 300 may be as optical computing device 106 (cf. FIG. 1). Accordingly, liquid or gas 302 may include a hydrocarbon product extracted from reservoir 150 and transferred from production pipeline 103 to contractor pipeline 105 by LACT system 108 (cf. FIG. 1).

Although not specifically shown, one or more processing elements may be employed in optical computing device 300 to restrict the optical wavelengths and/or bandwidths of the system, thereby eliminating unwanted electromagnetic radiation in wavelength regions that have no importance. Such processing elements can be located anywhere along the optical train, such as directly after a light source that provides the initial electromagnetic radiation.

Beams of electromagnetic radiation 304 and 306 impinge upon optical computing device 300, which includes ICE 100. In the illustrated embodiment ICE 100 may produce optically interacted light, for example, transmitted optically interacted light 310, and reflected optically interacted light 314. In operation, ICE 100 may be configured to distinguish electromagnetic radiation 304 from background electromagnetic radiation 306.

Transmitted optically interacted light 310, which may be related to the characteristic of interest of the liquid or gas 302, may be conveyed to a detector 312 for analysis and quantification. In some embodiments, detector 312 produces an output signal in the form of a voltage that corresponds to the particular characteristic of liquid or gas 302. In at least one embodiment, the signal produced by detector 312 and the characteristic of liquid or gas 302 (e.g., concentration of an analyte, or flow speed) may be directly proportional. In other embodiments, the relationship may be a polynomial function, an exponential function, and/or a logarithmic function. The reflected optically interacted light 314 may be related to other characteristics of the liquid or gas 302, and can be directed away from detector 312. In alternative configurations, ICE 100 is such that reflected optically interacted light 314 relates to the characteristic of interest, and the transmitted optically interacted light 310 relates to other characteristics in the liquid or gas 302.

In some embodiments, a second detector 316 can be present and arranged to detect the reflected optically interacted light 314. In other embodiments, second detector 316 may be arranged to detect electromagnetic radiation 304 and 306 derived from the liquid or gas 302 or electromagnetic radiation directed toward or before the liquid or gas 302. Without limitation, second detector 316 may be used to detect radiating deviations stemming from an electromagnetic radiation source (not shown), which provides the electromagnetic radiation (i.e., light) to the device 300. For example, radiating deviations can include such things as, but not limited to, intensity fluctuations in the electromagnetic radiation, interference fluctuations (e.g., dust or other interferences passing in front of the electromagnetic radiation source), coatings on windows included with optical computing device 300, combinations thereof, or the like. In some embodiments, optical computing device 300 may have the configuration of a beam splitter to separate electromagnetic radiation 304 and 306, and the transmitted or reflected electromagnetic radiation can then be directed to two or more ICEs 100. That is, in such embodiments, the transmitted or reflected electromagnetic radiation passes through ICE 100, which performs the computation before it travels to detector 312.

Some embodiments use a computer algorithm to estimate the impact of a component or contaminant, or a certain flow characteristic in liquid or gas 302 on the final pipeline flow composition. The algorithm may be part of an artificial neural network configured to use the concentration of each characteristic of interest in order to evaluate the overall characteristic(s) of the liquid or gas composition and predict the composition and/or concentration of fluid additives to provide for desired properties in the resultant pipeline flow. An artificial neural network can be trained using fluids of predetermined characteristics of interest, and thereby generating a virtual library. As the virtual library available to the artificial neural network becomes larger, the neural network can become more capable of accurately predicting the characteristic of interest corresponding to a liquid or gas or analyte thereof. Furthermore, with sufficient training the artificial neural network can more accurately predict the characteristics of the liquid or gas flow, even in the presence of unknown analytes.

In some embodiments, data collected using optical computing device 300 can be archived along with data associated with quality parameters being logged at or near a LACT system (e.g., LACT system 108, cf. FIG. 1). Evaluation of fluid transfer performance allows improvement of future operations and the planning of remedial action, if desired. In addition, the data and information can be communicated (wired or wirelessly) to a remote location by a communication system (e.g., satellite communication or wide area network communication) for further analysis. Automated control with a long-range communication system can further facilitate the performance of remote job operations. In particular, an artificial neural network facilitates the performance of remote job operations (e.g., via controller 110, cf. FIG. 1). In other embodiments, however, remote job operations can occur under direct operator control, where the operator is not at the job site (e.g., via wireless technology).

Figure 4A:
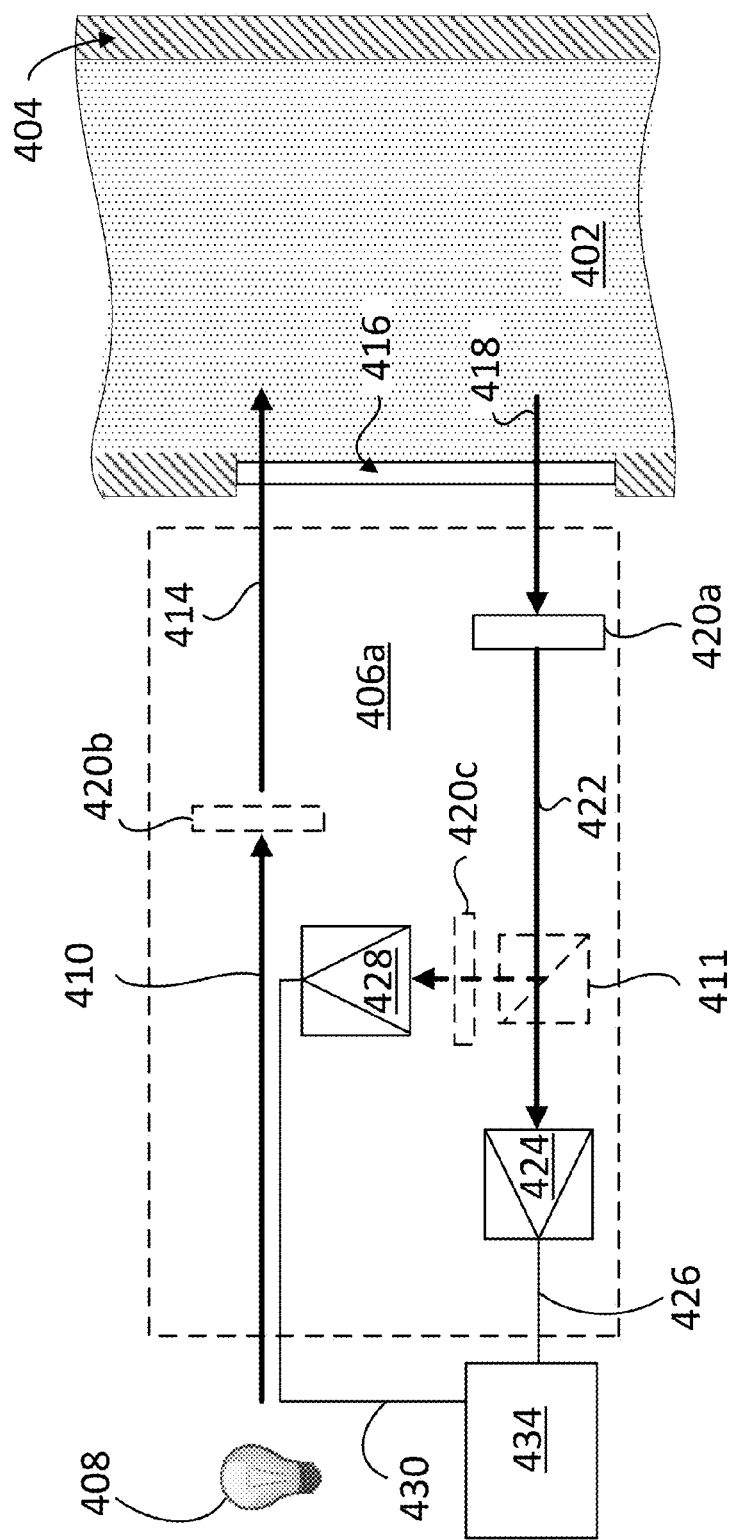
FIG. 4A illustrates an exemplary optical computing device for monitoring a fluid flow in a pipeline at or near a LACT point in a reflection configuration.

FIG. 4A illustrates an exemplary optical computing device 406a for monitoring a fluid 402 in a pipeline 404 at or near a LACT point (e.g., LACT system 108, cf. FIG. 1), in a reflection configuration. The fluid 402 may comprise a liquid or a gas contained within pipeline 404. A reflection configuration such as displayed in optical computing device 406a may be desirable when fluid 402 is an opaque liquid, such as crude oil. In at least one embodiment, pipeline 404 may be a production pipeline or a contractor pipeline (e.g., production pipeline 103 or contractor pipeline 105, cf. FIG. 1). In at least one embodiment, pipeline 404 may be a tank or container of a transport unit, such as a truck or a ship (e.g., truck 135, ship 137). In other embodiments pipeline 404 may be any other type of pipeline, as generally described or otherwise defined herein. For example, pipeline 404 may be part of a refinery or a power plant (e.g., refinery 137, power plant 139, cf. FIG. 1).

Optical computing device 406a may be similar in some respects to optical computing device 300 of FIG. 3 or optical computing device 106 of FIG. 1. While not shown, device 406a may be housed within a casing or housing configured to substantially protect the internal components of device 406a from damage or contamination from the external environment. The housing may couple device 406a to pipeline 404 mechanically with mechanical fasteners, threads, brazing or welding techniques, adhesives, magnets, combinations thereof or the like.

Optical computing device 406a may be useful in determining a particular characteristic of fluid 402 within pipeline 404, such as determining a concentration of an analyte present within fluid 402. The analyte of interest may be a contaminant or a substance that may affect a quality parameter of fluid 402. Knowledge of at least some of the characteristics of fluid 402 may help determine its overall composition. The resultant fluid flow transferred to a contractor pipeline may be of higher quality because the type and concentration of additives is tailored to a desired value at the LACT system.

In some embodiments, device 406a may include an electromagnetic radiation source 408 configured to emit or otherwise generate electromagnetic radiation 410. Electromagnetic radiation source 408 may be any device capable of emitting or generating electromagnetic radiation 410, as defined herein. For example, electromagnetic radiation source 408 may be a light bulb, a light emitting diode (LED), a laser, a blackbody emitter, a photonic crystal, an X-Ray source, combinations thereof, or the like. In some embodiments, a lens collects or otherwise receives electromagnetic radiation 410 and directs a beam 414 of electromagnetic radiation 410 toward fluid 402.

In one or more embodiments, device 406a may also include a sampling window 416 arranged adjacent to or otherwise in contact with fluid 402 for detection purposes. In some embodiments, sampling window 416 includes any one of a variety of transparent, rigid or semi-rigid materials that allow transmission of beam 414 therethrough. For example, sampling window 416 may include materials such as, but not limited to, glasses, plastics, semi-conductors, crystalline materials, sapphire, polycrystalline materials, hot or cold-pressed powders, combinations thereof, or the like.

After passing through sampling window 416, beam 414 impinges upon and optically interacts with fluid 402, including any analytes present within fluid 402. As a result, fluid 402 reflects or scatters back optically interacted radiation 418.

One or more ICEs 420a, 420b and 420c (hereinafter collectively referred to as ICEs 420) may be included in device 406a. ICE devices 420 may include spectral components substantially similar to ICE 100 described above with reference to FIGS. 1 and 2. In operation, ICE 420a receives optically interacted radiation 418 and produces modified electromagnetic radiation 422 corresponding to a particular characteristic of interest of fluid 402. Modified electromagnetic radiation 422 has optically interacted with ICE 420a which includes an approximate mimicking of a regression vector corresponding to the characteristic of interest of fluid 402. One of ordinary skill will recognize that any optical element may be used to direct beam 414 into fluid 402, to collect interacted radiation 418 from fluid 402, and to direct interacted radiation 418 through ICEs 420 into detector 424. Furthermore, one of ordinary skill recognizes that any of the optical elements in optical computing device 406a may be a free-space optical element such as a lens, a mirror, a prism, a polarizer, or any combination thereof, or a fiber optic component such as a beam splitter, a circulator, a wavelength division multiplexer, a collimator, or any combination thereof.

In some embodiments, ICE 420b (as shown in dashed lines) may alternatively be arranged within the optical train prior to sampling window 416 and equally obtain substantially the same results as ICE 420a. In other embodiments, sampling window 416 may serve a dual purpose as both a transmission window and a substrate for one of ICEs 420 (i.e., a spectral component). In yet other embodiments, ICE components 420 may generate modified electromagnetic radiation 422 through reflection, instead of transmission therethrough.

Embodiments consistent with the present disclosure may include at least two ICEs 420 in device 406a configured to cooperatively determine the characteristic of interest in fluid 402. For example, two or more ICE 420 arranged in series or in parallel within device 406a receive optically interacted radiation 418, thereby enhancing the sensitivity and the detection limit of device 406a. In some embodiments, two or more ICEs 420 may be arranged on a movable assembly, such as a rotating disc or an oscillating linear array, which moves such that individual ICEs 420 are exposed to or optically interacted with electromagnetic radiation 410 for a distinct brief period. Each of the two or more ICEs 420 in any of these embodiments may be associated or disassociated with the characteristic of interest in fluid 402. In other embodiments, each of the two or more ICEs 420 have a positive or a negative correlation with the characteristic of interest. Further, according to some embodiments, the two or more ICEs 420 may have opposite correlation with the characteristic of interest. In such embodiments, while a signal in detector 424 increases with an increase in the characteristic of interest for a first ICE 420, the signal in detector 424 decreases for a second ICE 420.

In some embodiments, it may be desirable to monitor more than one characteristic of interest at a time using device 406a. In such embodiments, various configurations for multiple ICEs can be used, where each ICE 420 is configured to detect a particular and/or distinct characteristic of interest corresponding, for example, to fluid 402 or to an analyte in the fluid 402. Some embodiments analyze the characteristic of interest sequentially using multiple ICEs interacting with a single beam of optically interacted radiation 418 reflected or backscattered from fluid 402. For example, some embodiments include multiple ICEs arranged on a rotating disc. In such embodiments, a beam of optically interacted radiation 418 interacts with an individual ICE 420 for a reduced time. Advantages of this approach can include the ability to analyze multiple characteristics of interest within fluid 402 using device 406a and the opportunity to assay additional characteristics simply by adding additional ICEs to the rotating disc corresponding to those additional characteristics.

Modified electromagnetic radiation 422 generated by ICE 420a is conveyed to detector 424 for quantification of the signal. Detector 424 may be any device capable of detecting electromagnetic radiation, such as an optical transducer. In some embodiments detector 424 is a thermal detector such as a thermopile or photo-acoustic detector, a semiconductor detector, a piezo-electric detector, a charge coupled device (CCD) detector, a video or array detector, a split detector, a photon detector (such as a photomultiplier tube), photodiodes, combinations thereof, or the like, or other detectors known to those skilled in the art.

In some embodiments, detector 424 may be configured to produce an output signal 426 in real-time or near real-time in the form of a voltage (or current) that corresponds to the particular characteristic of interest in fluid 402. Output signal 426 may be proportional to the dot product of the optically interacted radiation 418 with a regression vector associated with the characteristic of interest. As such, output signal 426 produced by detector 424 may be related to an amplitude or concentration of the characteristic of interest are related to one another. For example, output signal 426 may be directly proportional to the characteristic of interest. In other embodiments, however, the relationship may correspond to a polynomial function, an exponential function, a logarithmic function, and/or a combination thereof. In some embodiments, output signal 426 associated with ICE 420a may be negatively correlated with the characteristic of interest. Accordingly, output signal 426 decreases when the characteristic of interest increases.

In some embodiments, device 406a may include a second detector 428, which may be similar to first detector 424 in that it may be any device capable of detecting electromagnetic radiation. Similar to second detector 316 of FIG. 3, second detector 428 of FIG. 4A detects radiating deviations stemming from the electromagnetic radiation source 408. Accordingly, a beam splitter 411 (in dashes) may direct a portion of modified electromagnetic radiation 422 to detector 428, which may be configured to monitor radiating deviations in electromagnetic radiation source 408. In some embodiments, an ICE 420c (shown in dashes) before detector 428 modifies the electromagnetic radiation impinging on detector 428. Undesirable radiating deviations can occur in the intensity of the electromagnetic radiation 410 due to a wide variety of reasons, potentially causing various negative effects on the output of device 406a. These negative effects can be detrimental for measurements collected over an extended period of time. In some embodiments, radiating deviations can occur due to a build-up of a layer of residual material on the inside or outside of sampling window 416. This reduces the amount and quality of light ultimately reaching first detector 424. Without proper compensation, such radiating deviations could result in false readings and output signal 426 may inaccurately relate the characteristic of interest. In some embodiments, ICE 420c is used to provide complementary information about the characteristic of interest of the sample. For example, ICE 420c may have an opposite correlation with the characteristic of interest relative to ICE 420a. Further, in some embodiments ICE 420c may be disassociated with the characteristic of interest. In yet other embodiments, ICE 420c may be associated with a second characteristic of interest of the sample.

To compensate for these undesirable effects, second detector 428 generates a compensating signal 430 generally indicative of the radiating deviations of electromagnetic radiation source 408, thereby normalizing output signal 426 generated by first detector 424. In some embodiments, second detector 428 receives electromagnetic radiation from any portion of the optical train in device 406a to detect radiating deviations, without departing from the scope of the disclosure.

In some applications, output signal 426 and compensating signal 430 may be conveyed to or otherwise received by a signal processor 434 communicably coupled to both detectors 424, 428. Signal processor 434 may be part of a computer including a non-transitory machine-readable medium, configured to normalize output signal 426 using compensating signal 430, in view of any radiating deviations detected by second detector 428. Accordingly, signal processor 434 may be part of controller 110, such as processor 111 (cf. FIG. 1). In some embodiments, signal processor 434 computes a ratio or a difference of the two signals 426, 430. For example, the concentration or magnitude of each characteristic of interest determined using optical computing device 406a can be fed into an algorithm run by signal processor 434. The algorithm may be configured to make predictions on how the fluid 402 in combination with fluid additives, optionally at varying concentrations, will behave in a pipeline flow.

Those skilled in the art will readily recognize that, in one or more embodiments, electromagnetic radiation 410 derives from the fluid 402 itself. For example, various substances naturally radiate electromagnetic radiation that is able to interact with at least one ICE 420. In some embodiments, for example, fluid 402 or a substance within the fluid 402 may be a blackbody radiating substance configured to radiate heat that may optically interact with at least one of ICE components 420. In other embodiments, the fluid 402 or the substance within the fluid 402 may be radioactive or chemo-luminescent and emit electromagnetic radiation that is able to interact with ICE 420. In yet other embodiments, mechanical, magnetic, electric, actuation induces electromagnetic radiation from fluid 402 or from a substance within the fluid 402. For instance, in at least one embodiment, a voltage across fluid 402 or the substance within fluid 402 induces the electromagnetic radiation. As a result, in embodiments contemplated herein the electromagnetic radiation source 408 may be omitted from the particular optical computing device.

Figure 4B:
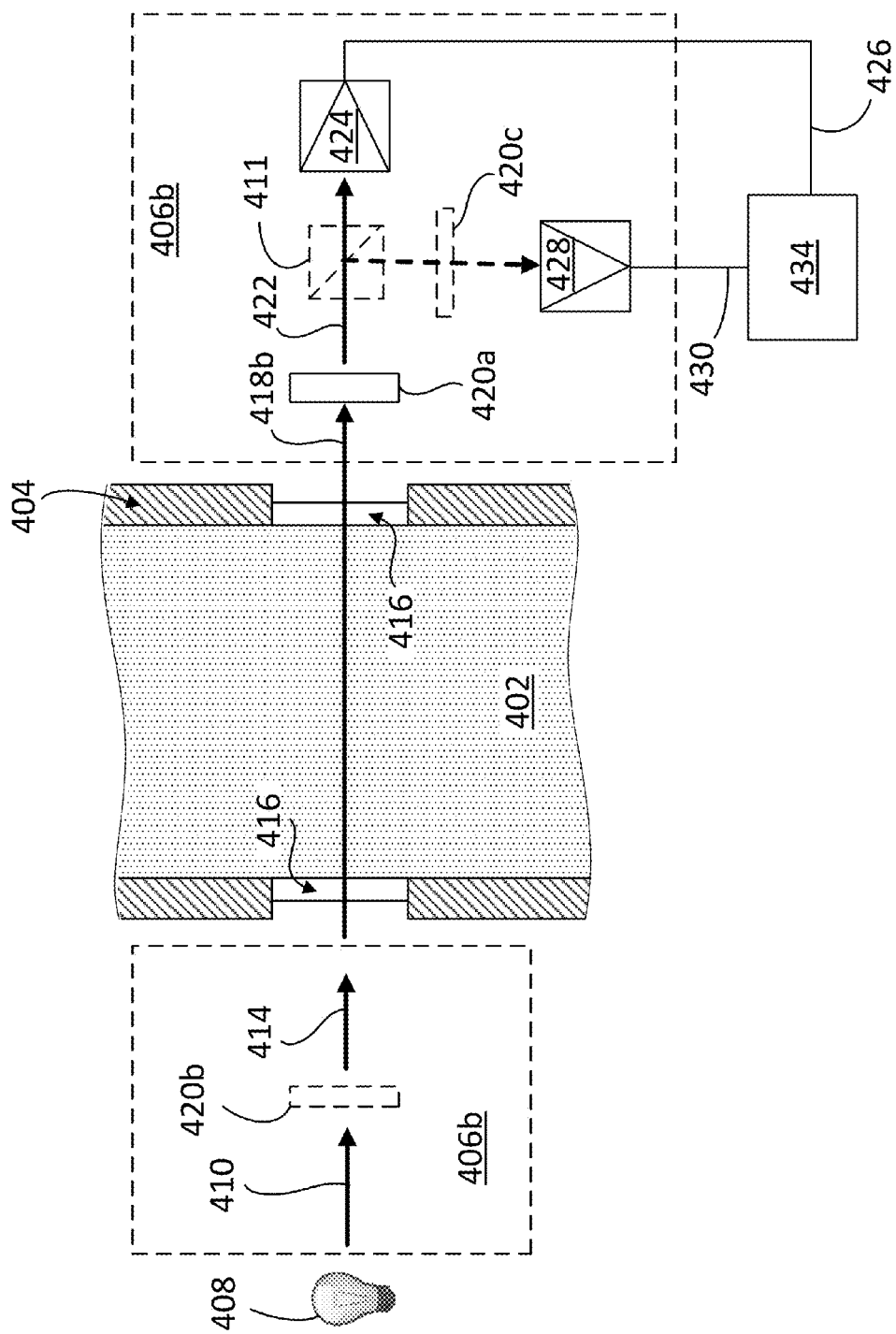
FIG. 4B illustrates an exemplary optical computing device for monitoring a fluid flow in a pipeline at or near a LACT point in a transmission configuration.

FIG. 4B illustrates an exemplary optical computing device 406b for monitoring a fluid flow 402 in a pipeline 404 at or near a LACT point (e.g., LACT system 108, cf. FIG. 1), in a transmission configuration. A transmission configuration such as displayed in optical computing device 406b may be desirable when fluid 402 is a transparent or semi-transparent liquid or gas, such as natural gas or gasoline. Beam 414 traverses a section of pipe 404, forming a transmitted radiation 418b that reaches detector 424. Without limitation, in some embodiments ICE 420a may be disposed in the optical train between an exit window 416 and detector 424. Accordingly, transmitted radiation 418b provides an aggregated or averaged value of a desired characteristic of fluid 402 across a portion of pipe 404. Other elements in FIG. 4B are as described above in reference to FIG. 4A, such as electromagnetic radiation source 408, electromagnetic radiation 410, sampling window 416, beam splitter 411, ICE 420c, modified electromagnetic radiation 422, detector 428, signals 426 and 430, and signal processor 434.

Figure 4C:
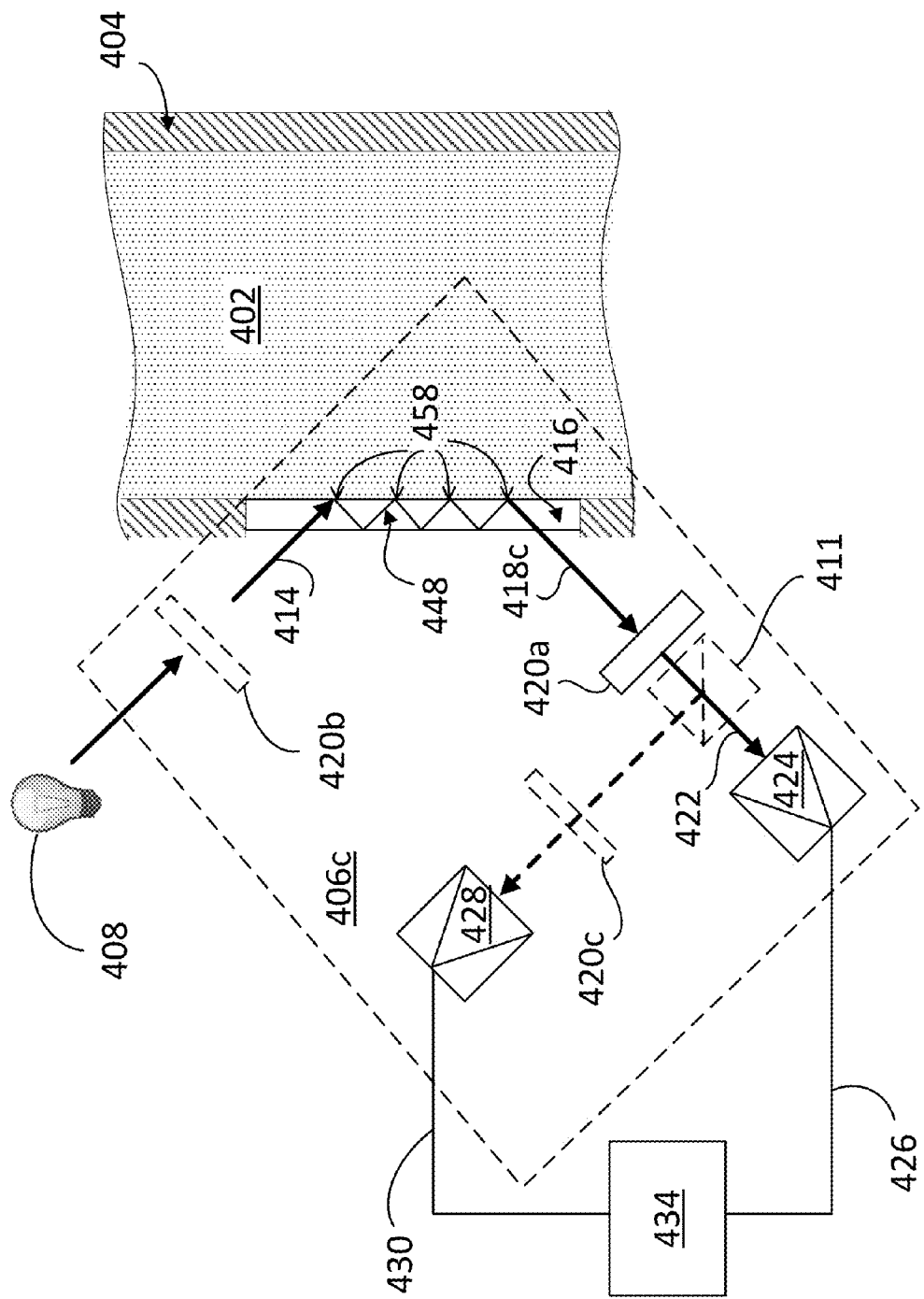
FIG. 4C illustrates an exemplary optical computing device for monitoring a fluid flow in a pipeline at or near a LACT point in a multiple reflection configuration.

FIG. 4C illustrates an exemplary optical computing device 406c for monitoring a fluid flow 402 in a pipeline 404 at or near a LACT point (e.g., LACT system 108, cf. FIG. 1), in a multiple reflection configuration. A multiple reflection configuration such as displayed in optical computing device 406c may be desirable when the fluid 402 is an opaque liquid, a dense liquid (e.g., crude oil) or a dense gas. Beam 414 impinges on window 416 at an angle such that a multiple internal reflection path 448 is formed across a portion of window 416. A beam 418c reflected multiple times on its interior side exits window 416 and reaches detector 424. Without limitation, in some embodiments, ICE 420a is disposed in the optical train between window 416 and detector 424. Multiply reflected beam 448 carries information about fluid 402 aggregated along a plurality of reflection points 458 on the interior side of window 416. Other elements in FIG. 4C are as described above in reference to FIGS. 4A-B, such as electromagnetic radiation source 408, electromagnetic radiation 410, sampling window 416, beam splitter 411, ICE 420c, modified electromagnetic radiation 422, detector 428, signals 426 and 430, and signal processor 434.

Figure 5:
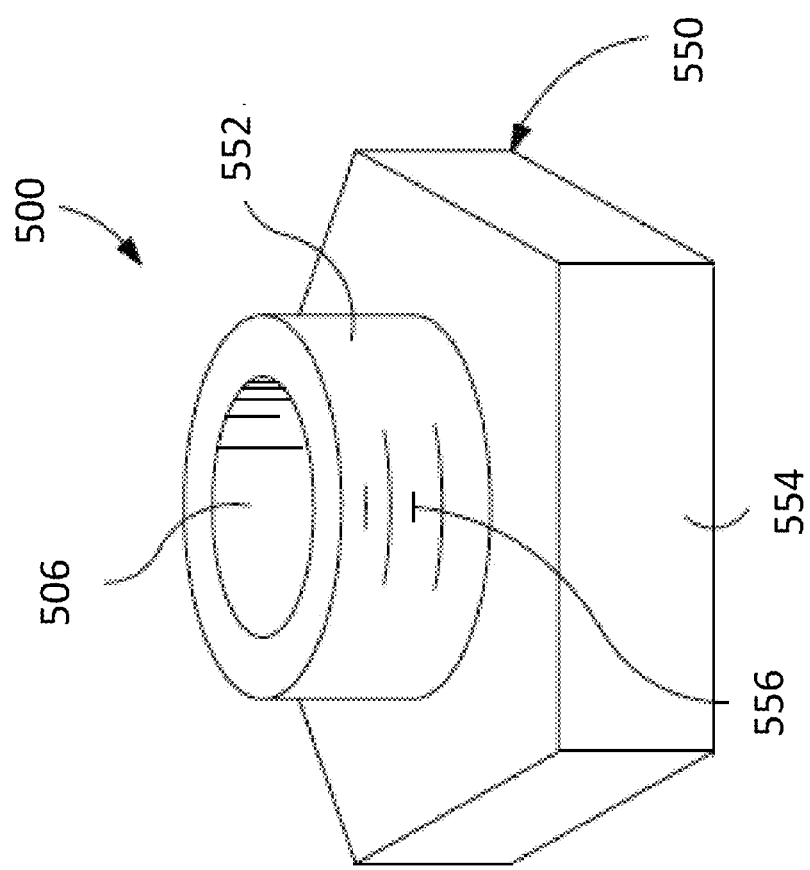
FIG. 5 illustrates an exemplary housing that may be used for an optical computing device.

FIG. 5 illustrates an exemplary housing 500 that may be used to house an optical computing device 506. In some embodiments, housing 500 may be mechanically coupled to a pipeline (e.g., production pipeline 103 or pipeline 404, cf. FIGS. 1 and 4A-C) using, for example, mechanical fasteners, brazing or welding techniques, adhesives, magnets, combinations thereof or the like. Housing 500 substantially protects the internal components of device 506 from damage or contamination from the external environment. Those skilled in the art, however, will readily recognize that several alternative designs and configurations of housings used to house the optical computing devices are suitable for the presently disclosed systems and methods. Indeed, housing embodiments described and disclosed herein are by way of example only, and should not limit the scope to the exemplary systems and methods disclosed herein.

As illustrated, housing 500 may be in the general form of a bolt 550 enclosing the various components of optical computing device 506. Optical computing device 506 may be as any one of optical computing device 106 of FIG. 1, or optical computing devices 406a-c of FIGS. 4A-C. In one embodiment, components of device 506 housed may be generally housed within a stem 552 of bolt 550, and bolt 550 may have a hex head 554 for manual manipulation of housing 500 using, for example, a wrench or other suitable torque-generating hand tool.

In at least one embodiment, housing 500 defines external threads 556 compatible with corresponding mating pipe threads provided in, for example, an opening defined in the pipeline that is configured to receive housing 500. A thread sealant between threads 556 and the mating pipe threads may prevent leakage of moisture or any undesirable substance through the juncture between housing 500 and the pipe.

Figure 6:
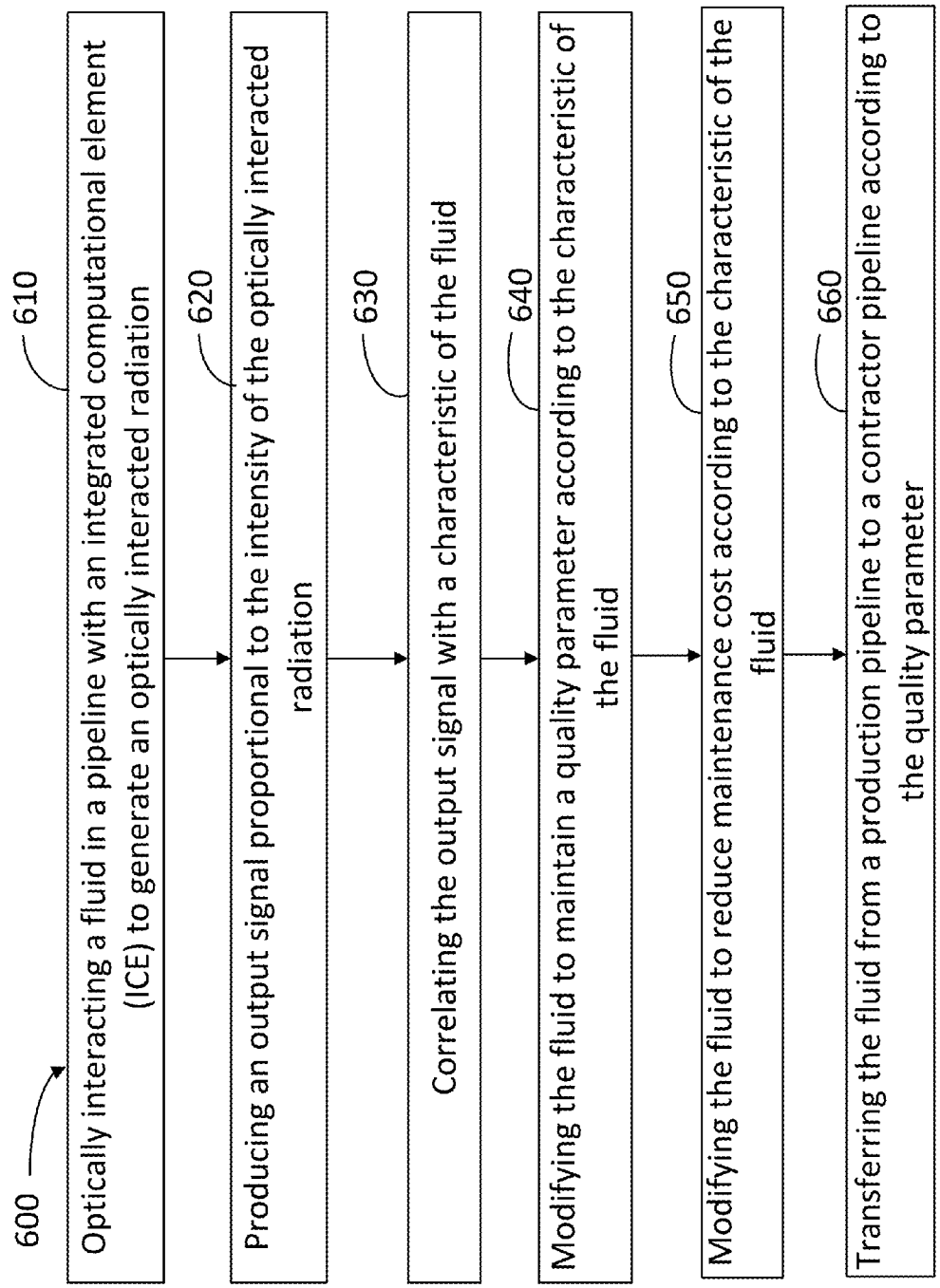
FIG. 6 illustrates a flowchart including steps in a method for monitoring a fluid during LACT.

FIG. 6 illustrates a flowchart including steps in a method 600 for monitoring a fluid during LACT. The fluid in method 600 may be a liquid, a gas, or any combination thereof, as disclosed in detail heretofore. Steps in method 600 may be at least partially performed by a controller having a processor and a memory (e.g., controller 110, processor 111, and memory 112, cf. FIG. 1). The controller communicatively coupled with an optical computing device and a LACT system separating a production pipeline from a contractor pipeline in an oil and gas production configuration (e.g., optical computing devices 106, 406, and 506, LACT system 108, production pipeline 103, contractor pipeline 105, and oil and gas production configuration 10, cf. FIGS. 1, 4A-C, and 5). Accordingly, the processor may be configured to execute commands stored in the memory, causing the controller to perform at least some of the steps in method 600. The oil and gas production configuration may include a bulk phase separator to separate a liquid from a gas in the fluid and a holding tank to inject a continuous flow into the production pipeline (e.g., bulk phase separator 121, holding tank 123, cf. FIG. 1). Furthermore, the LACT system in methods consistent with method 600 may include any one of a pump, a compressor, a heater, a cooler, a gas condenser, a shut-off valve to stop fluid flow from the production pipeline to the contractor pipeline, and a recycle valve to direct fluid flow to a recycle path. Furthermore, the LACT system may include a water removing station or a bubble removing station as part of a fluid recycling station. An optical computing device as disclosed herein may include at least one ICE associated with a desired characteristic of the fluid, and one ICE disassociated with the desired characteristic of the fluid (e.g., ICE 100, ICEs 420, cf. FIGS. 1 and 4A-C).

In some embodiments, a method for monitoring a fluid flow may include some, but not all of the steps in method 600, performed in a different sequence. Furthermore, a method consistent with the present disclosure may include at least some of the steps in method 600 performed overlapping in time, or almost simultaneously in time.

Step 610 includes optically interacting the fluid in the production pipeline with the ICE in the optical computing device to generate an optically interacted radiation. In some embodiments, step 610 includes providing an electromagnetic radiation with an electromagnetic radiation source. In some embodiments, step 610 may include using an electromagnetic radiation internally generated within the fluid, or externally generated by a natural source (e.g., sunlight). Step 610 may include interacting the electromagnetic radiation with the fluid in one of a transmission interaction, a reflection interaction, or a multiple internal reflection interaction with a sampling window adjacent to the fluid.

Step 620 includes producing an output signal proportional to the intensity of the optically interacted radiation. The output signal may be a voltage signal produced from a detector receiving the optically interacted radiation in the optical computing device.

Step 630 includes correlating the output signal with a characteristic of the fluid. In some embodiments, step 630 may include using a signal processor coupled to the optical computing device and configured to receive the output signal from the detector. Further, in step 630 the processor may be configured to perform a linear regression algorithm, or a nonlinear algorithm such as a neural network algorithm. The commands for performing the correlation in step 630 may be stored in the memory of the controller coupled to the optical computing device, consistent with embodiments disclosed herein.

Step 640 includes modifying the fluid to maintain a quality parameter according to the characteristic of the fluid. In some embodiments, step 640 further includes selecting the quality parameter according to an environmental characteristic of the production pipeline or the contractor pipeline, such as a seasonal temperature condition. In some embodiments, step 640 further includes selecting the quality parameter according to a destination of the fluid in the pipeline. For example, when the fluid is a natural gas and the destination is a power plant, step 640 may include selecting a BTU content of the natural gas according to a specification of the power plant operator. Likewise, when the fluid is liquid crude oil and the destination is a refinery, step 640 may include selecting a GOR in the crude oil according to a specification of the refinery operator.

In some embodiments, step 640 further includes a natural gas and the method further includes selecting the quality parameter according to a desired heat released by a combustion of the natural gas. In some embodiments, modifying the fluid to maintain a quality parameter includes redirecting the fluid to a cooling station to remove a liquid from a natural gas in the fluid. For example, in some embodiments modifying the fluid in step 640 includes removing a component from the fluid having a high dew temperature when the fluid is a gas flow. In some embodiments the gas may be a natural gas. Likewise, in some embodiments modifying the fluid in step 640 includes removing a component from the fluid having a low bubble temperature, when the fluid is a liquid. In some embodiments the liquid is a crude oil.

In some embodiments, modifying the fluid to maintain a quality parameter includes redirecting the fluid to the water removing station in the LACT system. In some embodiments, modifying the fluid to maintain a quality parameter includes redirecting the fluid to the bubble removing station in the LACT system. More generally, step 640 may include shutting off a valve into the contracting pipe and transferring the fluid to the recycling station in the LACT system when the quality parameter is not according to a specified value.

Step 650 includes modifying the fluid to reduce a maintenance cost according to the characteristic of the fluid. For example, in some embodiments the fluid is liquid crude oil and step 650 may include determining that a vapor pressure of the crude oil is higher than specified for the safe and clean operation of the contractor pipeline. Likewise, in some embodiments the fluid may be a natural gas flow and step 650 may include determining that a dew point of a component in the natural gas is higher than specified for the safe and clean operation of the contractor pipeline.

Step 660 includes transferring the fluid from a production pipeline to a contractor pipeline according to the quality parameter. In some embodiments, step 660 may include transferring the fluid to a destination point such as a transportation vehicle (a tanker ship or a tanker truck), a refinery, or a power station.

Embodiments disclosed herein include:

A. A device including an integrated computational element (ICE) positioned to optically interact with electromagnetic radiation from a fluid. The device is configured to generate optically interacted radiation corresponding to a characteristic of the fluid. The device may include a detector positioned to receive the optically interacted radiation and to generate an output signal proportional to an intensity of the optically interacted radiation, and a processor positioned to receive the output signal and to determine the characteristic of the fluid. The device may be coupled to a controller configured to provide instructions to a transfer system for storage and readout.

B. A method including optically interacting a fluid in a production pipeline with an integrated computational element (ICE) to generate an optically interacted radiation. The method also includes producing an output signal proportional to an intensity of the optically interacted radiation, correlating the output signal with a characteristic of the fluid, modifying the fluid to maintain a quality parameter according to the characteristic of the fluid, and transferring the fluid from a production pipeline to a contractor pipeline according to the quality parameter.

C. A non-transitory, computer readable medium storing commands which, when executed by a processor in a measurement system including an optical computing device cause the measurement system to perform a method including optically interacting a fluid in a production pipeline with an integrated computational element (ICE) to generate an optically interacted radiation; producing an output signal proportional to an intensity of the optically interacted radiation. The method also includes correlating the output signal with a characteristic of the fluid, modifying the fluid to maintain a quality parameter according to the characteristic of the fluid and to reduce a maintenance cost according to the characteristic of the fluid, and transferring the fluid from a production pipeline to a contractor pipeline according to the quality parameter.

Each of embodiments A, B, and C may have one or more of the following additional elements in any combination.

Element 1, wherein the transfer system is a lease automatic custody transfer (LACT) system positioned upstream from a contractor pipeline in an oil and gas production configuration, and the LACT system is configured to modify a flow and composition of the fluid when the characteristic of the fluid is below a quality parameter. Element 2, wherein the fluid includes liquid crude oil and the ICE is configured to detect a contaminant in the liquid crude oil, the contaminant including a residual additive for oil production, water, or natural gas. Element 3, wherein the fluid includes natural gas and the ICE is configured to detect methane, propane, water, or entrained liquid. Element 4, wherein the quality parameter is selected according to an environmental characteristic of the pipeline. Element 5, wherein the quality parameter is selected according to a destination of the fluid in the pipeline. Element 6, wherein the fluid includes natural gas and the quality parameter is selected according to a heat value released by combustion of the natural gas. Element 7, further including a first optical element to direct an incident light through a sampling window in the pipeline and a second optical element to collect the optically interacted radiation reflected from the fluid in the pipeline. Element 8, further including a first optical element to direct an incident electromagnetic radiation through a sampling window in the pipeline and a second optical element to collect the optically interacted radiation transmitted through the fluid in the pipeline. Element 9, further including a first optical element to direct an incident electromagnetic radiation through a sampling window in the pipeline and a second optical element to collect the optically interacted radiation reflected multiple times on a side of the sampling window in contact with the fluid in the pipeline.

Element 10, wherein modifying the fluid includes modifying the fluid to reduce a maintenance cost according to the characteristic of the fluid. Element 11, further including selecting the quality parameter according to an environmental characteristic of one of the production pipeline or the contractor pipeline. Element 12, further including selecting the quality parameter according to a destination of the fluid in one of the production pipeline or the contractor pipeline. Element 13, wherein the fluid includes a natural gas and the method further includes selecting the quality parameter according to a desired heat released by a combustion of the natural gas. Element 14, wherein modifying the fluid to maintain a quality parameter includes redirecting the fluid to a recycle station to remove a liquid from a natural gas in the fluid. Element 15, wherein modifying the fluid to maintain a quality parameter includes redirecting the fluid to a water removing station. Element 16, wherein modifying the fluid to maintain a quality parameter includes redirecting the fluid to a bubble removing station.

Element 17, wherein the fluid includes a natural gas and the method further includes selecting the quality parameter according to a desired heat released by a combustion of the natural gas.

By way of non-limiting example, exemplary combinations applicable to A, B, and C include Element 1 with Element 2, Element 11 with Element 12, and Element 13 with Element 17.

It is recognized that the various embodiments herein directed to computer control and artificial neural networks, including various blocks, modules, elements, components, methods, and algorithms, can be implemented using computer hardware, software, combinations thereof, and the like. To illustrate this interchangeability of hardware and software, various illustrative blocks, modules, elements, components, methods and algorithms have been described generally in terms of their functionality. Whether such functionality is implemented as hardware or software will depend upon the particular application and any imposed design constraints. For at least this reason, it is to be recognized that one of ordinary skill in the art can implement the described functionality in a variety of ways for a particular application. Further, various components and blocks can be arranged in a different order or partitioned differently, for example, without departing from the scope of the embodiments expressly described.

Computer hardware used to implement the various illustrative blocks, modules, elements, components, methods, and algorithms described herein can include a processor configured to execute one or more sequences of instructions, programming stances, or code stored on a non-transitory, computer-readable medium. The processor can be, for example, a general purpose microprocessor, a microcontroller, a digital signal processor, an application specific integrated circuit, a field programmable gate array, a programmable logic device, a controller, a state machine, a gated logic, discrete hardware components, an artificial neural network, or any like suitable entity that can perform calculations or other manipulations of data. In some embodiments, computer hardware can further include elements such as, for example, a memory (e.g., random access memory (RAM), flash memory, read only memory (ROM), programmable read only memory (PROM), erasable read only memory (EPROM)), registers, hard disks, removable disks, CD-ROMS, DVDs, or any other like suitable storage device or medium.

Executable sequences described herein can be implemented with one or more sequences of code contained in a memory. In some embodiments, such code can be read into the memory from another machine-readable medium. Execution of the sequences of instructions contained in the memory can cause a processor to perform the process steps described herein. One or more processors in a multi-processing arrangement can also be employed to execute instruction sequences in the memory. In addition, hard-wired circuitry can be used in place of or in combination with software instructions to implement various embodiments described herein. Thus, the present embodiments are not limited to any specific combination of hardware and/or software.

As used herein, a machine-readable medium will refer to any medium that directly or indirectly provides instructions to a processor for execution. A machine-readable medium can take on many forms including, for example, non-volatile media, volatile media, and transmission media. Non-volatile media can include, for example, optical and magnetic disks. Volatile media can include, for example, dynamic memory. Transmission media can include, for example, coaxial cables, wire, fiber optics, and wires that form a bus. Common forms of machine-readable media can include, for example, floppy disks, flexible disks, hard disks, magnetic tapes, other like magnetic media, CD-ROMs, DVDs, other like optical media, punch cards, paper tapes and like physical media with patterned holes, RAM, ROM, PROM, EPROM, and flash EPROM.

The exemplary embodiments described herein are well adapted to attain the ends and advantages mentioned as well as those that are inherent therein. The particular embodiments disclosed above are illustrative only, as the exemplary embodiments described herein may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope and spirit of the present disclosure. The disclosure illustratively disclosed herein suitably may be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the element that it introduces. If there is any conflict in the usages of a word or term in this specification and one or more patent or other documents that may be incorporated herein by reference, the definitions that are consistent with this specification should be adopted.

As used herein, the phrase "at least one of" preceding a series of items, with the terms "and" or "or" to separate any of the items, modifies the list as a whole, rather than each member of the list (i.e., each item). The phrase "at least one of" does not require selection of at least one item; rather, the phrase allows a meaning that includes at least one of any one of the items, and/or at least one of any combination of the items, and/or at least one of each of the items. By way of example, the phrases "at least one of X, Y, and Z" or "at least one of X, Y, or Z" each refer to only X, only Y, or only Z; any combination of X, Y, and Z; and/or at least one of each of X, Y, and Z.

The disclosure claimed is:

1. A device comprising:
    an integrated computational element (ICE) positioned to optically interact with electromagnetic radiation from a fluid and to thereby generate optically interacted radiation corresponding to a characteristic of the fluid, wherein the fluid comprises a hydrocarbon product;
    a detector positioned to receive the optically interacted radiation and to generate an output signal proportional to an intensity of the optically interacted radiation; and
    a processor positioned to receive the output signal and to determine the characteristic of the fluid, and to determine a value of a quality parameter of the hydrocarbon product based on the characteristic of the fluid, wherein the device is coupled to a controller configured to provide instructions to a transfer system for storage and readout, and to modify a fluid flow parameter based on the quality parameter, and wherein to modify the fluid flow parameter comprises to redirect the fluid.

2. The device of claim 1, wherein the transfer system is a lease automatic custody transfer (LACT) system positioned upstream from a contractor pipeline in an oil and gas production configuration, and the LACT system is configured to modify a flow and composition of the fluid when the characteristic of the fluid is below the quality parameter.

3. The device of claim 1, wherein the fluid includes liquid crude oil and the ICE is configured to detect a contaminant in the liquid crude oil, the contaminant including a residual additive for oil production, water, or natural gas.

4. The device of claim 1, wherein the fluid includes natural gas and the ICE is configured to detect methane, propane, water, or entrained liquid.

5. The device of claim 1, wherein the characteristic of the fluid comprises a quality parameter selected according to an environmental characteristic of a pipeline.

6. The device of claim 1, wherein the characteristic of the fluid comprises a quality parameter selected according to a destination of the fluid in a pipeline.

7. The device of claim 1, wherein the fluid includes natural gas and the quality parameter is selected according to a heat value released by combustion of the natural gas.

8. The device of claim 1, further including a first optical element to direct an incident light through a sampling window in a pipeline and a second optical element to collect the optically interacted radiation reflected from the fluid in the pipeline.

9. The device of claim 1, further including a first optical element to direct an incident electromagnetic radiation through a sampling window in a pipeline and a second optical element to collect the optically interacted radiation transmitted through the fluid in the pipeline.

10. The device of claim 1, further including a first optical element to direct an incident electromagnetic radiation through a sampling window in a pipeline and a second optical element to collect an optically interacted radiation reflected multiple times on a side of the sampling window in contact with the fluid in the pipeline.

11. A method comprising:
    optically interacting a fluid in a production pipeline with an integrated computational element (ICE) to generate an optically interacted radiation, wherein the fluid comprises a hydrocarbon product;

obtaining, with a detector, a detector signal from the optically interacted radiation, wherein the detector signal is proportional to an intensity of the optically interacted radiation;

producing, with a processor, an output signal from the detector signal based on a regression vector associated with a characteristic of the fluid;

correlating the output signal with a quality parameter of the hydrocarbon product based on a characteristic of the fluid;

modifying the fluid to maintain a quality parameter according to the quality parameter, wherein modifying the fluid comprises redirecting the fluid; and transferring the fluid from a production pipeline to a contractor pipeline according to the quality parameter.

12. The method of claim 11, wherein modifying the fluid includes modifying the fluid to reduce a maintenance cost according to the characteristic of the fluid.

13. The method of claim 11, further including selecting the quality parameter according to an environmental characteristic of one of the production pipeline or the contractor pipeline.

14. The method of claim 11, further including selecting the quality parameter according to a destination of the fluid in one of the production pipeline or the contractor pipeline.

15. The method of claim 11, wherein the fluid includes a natural gas and the method further includes selecting the quality parameter according to a desired heat released by a combustion of the natural gas.

16. The method of claim 11, wherein modifying the fluid to maintain a quality parameter includes redirecting the fluid to a recycle station to remove a liquid from a natural gas in the fluid.

17. The method of claim 11, wherein modifying the fluid to maintain a quality parameter includes redirecting the fluid to a water removing station.

18. The method of claim 11, wherein modifying the fluid to maintain a quality parameter includes redirecting the fluid to a bubble removing station.

19. A non-transitory, computer readable medium storing commands which, when executed by a processor in a measurement system including an optical computing device cause the measurement system to perform a method comprising:

optically interacting a fluid in a production pipeline with an integrated computational element (ICE) to generate an optically interacted radiation, wherein the fluid comprises a hydrocarbon product;

obtaining, with a detector, a detector signal from the optically interacted radiation, wherein the detector signal is proportional to an intensity of the optically interacted radiation;

producing, with a processor, an output signal from the detector signal based on a regression vector associated with a characteristic of the fluid;

correlating the output signal with a quality parameter of the hydrocarbon product based on a characteristic of the fluid;

modifying the fluid to maintain a quality parameter according to the quality parameter and to reduce a maintenance cost according to the characteristic of the fluid, wherein modifying the fluid comprises redirecting the fluid; and transferring the fluid from a production pipeline to a contractor pipeline according to the quality parameter.

20. The non-transitory, computer readable medium of claim 19, wherein the fluid includes a natural gas and the method further includes selecting the quality parameter according to a desired heat released by a combustion of the natural gas.

* * * * *